(12) United States Patent
Sharkawy et al.

(10) Patent No.: US 7,503,930 B2
(45) Date of Patent: *Mar. 17, 2009

(54) PROSTHETIC CARDIAC VALVES AND SYSTEMS AND METHODS FOR IMPLANTING THEREOF

(75) Inventors: Adam Sharkawy, San Jose, CA (US);
Mark Foley, Menlo Park, CA (US);
Darin Gittings, Sunnyvale, CA (US);
David Cole, San Mateo, CA (US); Sam Crews, Palo Alto, CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/707,331

(22) Filed: Feb. 16, 2007

(65) Prior Publication Data

US 2007/0162113 A1    Jul. 12, 2007

Related U.S. Application Data

(63) Continuation of application No. 11/003,693, filed on Dec. 3, 2004, now Pat. No. 7,186,265.

(60) Provisional application No. 60/528,620, filed on Dec. 10, 2003.

(51) Int. Cl.
*A61F 2/24* (2006.01)

(52) U.S. Cl. .................... 623/2.11; 623/2.38

(58) Field of Classification Search .......... 623/2.1–2.42
See application file for complete search history.

(56) References Cited

U.S. PATENT DOCUMENTS

| 3,334,629 A | 8/1967 | Cohn |
| 3,540,431 A | 11/1970 | Mobin-Uddin |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,795,246 A | 3/1974 | Sturgeon |
| 3,839,741 A | 10/1974 | Haller |
| 3,868,956 A | 3/1975 | Alfidi et al. |

(Continued)

FOREIGN PATENT DOCUMENTS

EP        1057459        12/2000

(Continued)

OTHER PUBLICATIONS

Andersen, H.R. et al, "Transluminal implantation of artificial heart valves. Description of a new expandable aortic valve and initial results with implantation by catheter technique in closed chest pigs." Euro. Heart J. (1992) 13:704-708.

(Continued)

*Primary Examiner*—Suzette J Gherbi
(74) *Attorney, Agent, or Firm*—Mike Jaro; Jeffrey J. Hohenshell (57) ABSTRACT

Implantable prosthetic valve systems and methods for implanting them are provided. Magnets are employed within one or more components of the valve systems to facilitate anchoring of the prosthetic valve at a target implant site, delivery of the prosthetic valve to the target implant site or both.

7 Claims, 6 Drawing Sheets

U.S. PATENT DOCUMENTS

| | | |
|---|---|---|
| 3,874,388 A | 4/1975 | King et al. |
| 4,056,854 A | 11/1977 | Boretos et al. |
| 4,106,129 A | 8/1978 | Carpentier et al. |
| 4,233,690 A | 11/1980 | Akins |
| 4,291,420 A | 9/1981 | Reul |
| 4,425,908 A | 1/1984 | Simon |
| 4,501,030 A | 2/1985 | Lane |
| 4,580,568 A | 4/1986 | Gianturco |
| 4,610,688 A | 9/1986 | Silvestrini et al. |
| 4,647,283 A | 3/1987 | Carpentier et al. |
| 4,648,881 A | 3/1987 | Carpentier et al. |
| 4,655,771 A | 4/1987 | Wallsten |
| 4,662,885 A | 5/1987 | DiPisa, Jr. |
| 4,665,906 A | 5/1987 | Jervis |
| 4,710,192 A | 12/1987 | Liotta et al. |
| 4,733,665 A | 3/1988 | Palmaz |
| 4,819,751 A | 4/1989 | Shimada et al. |
| 4,820,299 A | 4/1989 | Philippe et al. |
| 4,834,755 A | 5/1989 | Silvestrini et al. |
| 4,856,516 A | 8/1989 | Hillstead |
| 4,872,874 A | 10/1989 | Taheri |
| 4,909,252 A | 3/1990 | Goldberger |
| 4,917,102 A | 4/1990 | Miller et al. |
| 4,954,126 A | 9/1990 | Wallsten |
| 4,994,077 A | 2/1991 | Dobben |
| 5,002,559 A | 3/1991 | Tower |
| 5,161,547 A | 11/1992 | Tower |
| 5,217,483 A | 6/1993 | Tower |
| 5,332,402 A | 7/1994 | Teitelbaum et al. |
| 5,350,398 A | 9/1994 | Pavcnik et al. |
| 5,370,685 A | 12/1994 | Stevens |
| 5,389,106 A | 2/1995 | Tower |
| 5,397,351 A | 3/1995 | Pavcnik et al. |
| 5,411,552 A | 5/1995 | Andersen et al. |
| 5,431,676 A | 7/1995 | Dubrul et al. |
| 5,507,767 A | 4/1996 | Maeda et al. |
| 5,545,211 A | 8/1996 | An et al. |
| 5,554,185 A | 9/1996 | Block et al. |
| 5,575,818 A | 11/1996 | Pinchuk |
| 5,645,559 A | 7/1997 | Hachtman et al. |
| 5,667,523 A | 9/1997 | Bynon et al. |
| 5,674,277 A | 10/1997 | Freitag |
| 5,695,498 A | 12/1997 | Tower |
| 5,713,953 A | 2/1998 | Vallana et al. |
| 5,800,456 A | 9/1998 | Maeda et al. |
| 5,817,126 A | 10/1998 | Imran |
| 5,824,043 A | 10/1998 | Cottone, Jr. |
| 5,824,053 A | 10/1998 | Khosravi et al. |
| 5,824,056 A | 10/1998 | Rosenberg |
| 5,824,064 A | 10/1998 | Taheri |
| 5,840,081 A | 11/1998 | Andersen et al. |
| 5,855,597 A | 1/1999 | Jayaraman |
| 5,855,601 A | 1/1999 | Bessler et al. |
| 5,860,966 A | 1/1999 | Tower |
| 5,861,028 A | 1/1999 | Angell |
| 5,868,783 A | 2/1999 | Tower |
| 5,876,448 A | 3/1999 | Thompson et al. |
| 5,888,201 A | 3/1999 | Stinson et al. |
| 5,891,191 A | 4/1999 | Stinson |
| 5,907,893 A | 6/1999 | Zadno-Azizi et al. |
| 5,925,063 A | 7/1999 | Khosravi |
| 5,944,738 A | 8/1999 | Amplatz et al. |
| 5,954,766 A | 9/1999 | Zadno-Azizi et al. |
| 5,957,949 A | 9/1999 | Leonhardt et al. |
| 5,984,957 A | 11/1999 | Laptewicz, Jr. et al. |
| 6,027,525 A | 2/2000 | Suh et al. |
| 6,042,598 A | 3/2000 | Tsugita et al. |
| 6,051,014 A | 4/2000 | Jang |
| 6,123,723 A | 9/2000 | Konya et al. |
| 6,146,366 A | 11/2000 | Schachar |
| 6,162,245 A | 12/2000 | Jayaraman |
| 6,168,614 B1 | 1/2001 | Andersen et al. |
| 6,200,336 B1 | 3/2001 | Pavcnik et al. |
| 6,221,006 B1 | 4/2001 | Dubrul et al. |
| 6,221,091 B1 | 4/2001 | Khosravi |
| 6,241,757 B1 | 6/2001 | An et al. |
| 6,258,114 B1 | 7/2001 | Konya et al. |
| 6,258,115 B1 | 7/2001 | Dubrul |
| 6,258,120 B1 | 7/2001 | McKenzie et al. |
| 6,277,555 B1 | 8/2001 | Duran et al. |
| 6,327,772 B1 | 12/2001 | Zadno-Azizi et al. |
| 6,338,735 B1 | 1/2002 | Stevens |
| 6,348,063 B1 | 2/2002 | Yassour et al. |
| 6,350,282 B1 | 2/2002 | Eberhardt |
| 6,352,543 B1 | 3/2002 | Cole et al. |
| 6,352,708 B1 | 3/2002 | Duran et al. |
| 6,371,970 B1 | 4/2002 | Khosravi et al. |
| 6,371,983 B1 | 4/2002 | Lane |
| 6,379,383 B1 | 4/2002 | Palmaz et al. |
| 6,398,807 B1 | 6/2002 | Chouinard et al. |
| 6,409,750 B1 | 6/2002 | Hyodoh et al. |
| 6,425,916 B1 | 7/2002 | Garrison et al. |
| 6,440,164 B1 | 8/2002 | DiMatteo et al. |
| 6,458,153 B1 | 10/2002 | Bailey et al. |
| 6,468,303 B1 | 10/2002 | Amplatz et al. |
| 6,475,239 B1 | 11/2002 | Campbell et al. |
| 6,482,228 B1 | 11/2002 | Norred |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,517,558 B2 | 2/2003 | Gittings et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,562,058 B2 | 5/2003 | Seguin et al. |
| 6,569,196 B1 | 5/2003 | Vesely |
| 6,592,546 B1 | 7/2003 | Barbut et al. |
| 6,622,604 B1 | 9/2003 | Chouinard et al. |
| 6,632,243 B1 | 10/2003 | Zadno-Azizi et al. |
| 6,635,068 B1 | 10/2003 | Dubrul et al. |
| 6,635,214 B2 | 10/2003 | Rapacki et al. |
| 6,651,670 B2 | 11/2003 | Rapacki et al. |
| 6,652,540 B1 | 11/2003 | Cole et al. |
| 6,652,571 B1 | 11/2003 | White et al. |
| 6,652,578 B2 | 11/2003 | Bailey et al. |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,702,851 B1 | 3/2004 | Chinn et al. |
| 6,719,768 B1 | 4/2004 | Cole et al. |
| 6,719,789 B2 | 4/2004 | Cox |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,758,855 B2 | 7/2004 | Fulton, III et al. |
| 6,769,434 B2 | 8/2004 | Liddicoat et al. |
| 6,802,847 B1 | 10/2004 | Carson et al. |
| 6,808,498 B2 | 10/2004 | Laroya et al. |
| 6,887,266 B2 | 5/2005 | Williams et al. |
| 6,890,330 B2 | 5/2005 | Streeter et al. |
| 6,896,690 B1 | 5/2005 | Lambrecht et al. |
| 6,929,653 B2 | 8/2005 | Streeter |
| 6,932,827 B2 | 8/2005 | Cole et al. |
| 7,018,408 B2 * | 3/2006 | Bailey et al. ............... 623/2.11 |
| 7,025,773 B2 | 4/2006 | Gittings et al. |

| | | |
|---|---|---|
| 7,186,265 B2 | 3/2007 | Sharkawy |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0047197 A1 | 11/2001 | Foley et al. |
| 2002/0032480 A1 | 3/2002 | Spence et al. |
| 2002/0032481 A1 | 3/2002 | Gabbay |
| 2002/0052651 A1 | 5/2002 | Myers et al. |
| 2002/0058995 A1 | 5/2002 | Stevens |
| 2002/0077696 A1 | 6/2002 | Zadno-Azizi et al. |
| 2002/0095209 A1 | 7/2002 | Zadno-Azizi et al. |
| 2002/0111674 A1 | 8/2002 | Chouinard et al. |
| 2002/0123786 A1 | 9/2002 | Gittings et al. |
| 2002/0144696 A1 | 10/2002 | Sharkawy et al. |
| 2002/0151970 A1 | 10/2002 | Garrison et al. |
| 2002/0161392 A1 | 10/2002 | Dubrul |
| 2002/0161394 A1 | 10/2002 | Macoviak et al. |
| 2002/0193871 A1 | 12/2002 | Beyersdorf et al. |
| 2003/0014104 A1 | 1/2003 | Cribier |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0040771 A1 | 2/2003 | Hyodoh et al. |
| 2003/0040772 A1 | 2/2003 | Hyodoh et al. |
| 2003/0055495 A1 | 3/2003 | Pease et al. |
| 2003/0109924 A1 | 6/2003 | Cribier |
| 2003/0125795 A1 | 7/2003 | Pavcnik et al. |
| 2003/0130729 A1 | 7/2003 | Paniagua et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0158573 A1 | 8/2003 | Gittings et al. |
| 2003/0181850 A1 | 9/2003 | Diamond et al. |
| 2003/0199913 A1 | 10/2003 | Dubrul et al. |
| 2003/0199963 A1 | 10/2003 | Tower et al. |
| 2003/0199972 A1 | 10/2003 | Zadno-Azizi et al. |
| 2003/0212452 A1 | 11/2003 | Zadno-Azizi et al. |
| 2003/0212454 A1 | 11/2003 | Scott et al. |
| 2004/0039436 A1 | 2/2004 | Spenser et al. |
| 2004/0049224 A1 | 3/2004 | Buehlmann et al. |
| 2004/0049262 A1 | 3/2004 | Obermiller et al. |
| 2004/0049266 A1 | 3/2004 | Anduiza et al. |
| 2004/0082904 A1 | 4/2004 | Houde et al. |
| 2004/0088045 A1 | 5/2004 | Cox |
| 2004/0097988 A1 | 5/2004 | Gittings et al. |
| 2004/0098112 A1 | 5/2004 | DiMatteo et al. |
| 2004/0111096 A1 | 6/2004 | Tu et al. |
| 2004/0113306 A1 | 6/2004 | Rapacki et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0122516 A1 | 6/2004 | Fogarty et al. |
| 2004/0127979 A1 | 7/2004 | Wilson |
| 2004/0138742 A1 | 7/2004 | Myers et al. |
| 2004/0138743 A1 | 7/2004 | Myers et al. |
| 2004/0168691 A1 | 9/2004 | Sharkawy et al. |
| 2004/0186563 A1 | 9/2004 | Lobbi |
| 2004/0215339 A1 | 10/2004 | Drasler et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0096692 A1 | 5/2005 | Linder et al. |
| 2005/0096734 A1 | 5/2005 | Majercak et al. |
| 2005/0096735 A1 | 5/2005 | Hojeibane et al. |
| 2005/0096738 A1 | 5/2005 | Cali et al. |
| 2005/0209065 A1 | 9/2005 | Schlosser |
| 2005/0240263 A1 | 10/2005 | Fogarty et al. |
| 2006/0052867 A1 | 3/2006 | Revuelta et al. |
| 2006/0069400 A1 | 3/2006 | Burnett et al. |
| 2006/0195184 A1 | 8/2006 | Lane et al. |
| 2006/0195186 A1 | 8/2006 | Drews et al. |
| 2006/0229708 A1 | 10/2006 | Powell et al. |

FOREIGN PATENT DOCUMENTS

| | | |
|---|---|---|
| EP | 0937439 B1 | 9/2003 |
| EP | 1340473 | 9/2003 |
| EP | 1356793 | 10/2003 |
| EP | 0819013 | 6/2004 |
| EP | 1229864 B1 | 4/2005 |
| FR | 2 826 863 | 1/2003 |
| WO | WO 93/15693 | 8/1993 |
| WO | WO 95/04556 | 2/1995 |
| WO | WO 95/29640 | 11/1995 |
| WO | WO 96/14032 | 5/1996 |
| WO | WO 98/36790 | 8/1998 |
| WO | WO 00/09059 | 2/2000 |
| WO | WO 00/44308 | 8/2000 |
| WO | WO 00/44313 | 8/2000 |
| WO | WO 00/66009 | 11/2000 |
| WO | WO 00/67661 | 11/2000 |
| WO | WO 01/05331 | 1/2001 |
| WO | WO 01/35870 | 5/2001 |
| WO | WO 01/64137 | 9/2001 |
| WO | WO 02/36048 | 5/2002 |
| WO | WO 02/100297 | 12/2002 |
| WO | WO 03/003943 | 1/2003 |
| WO | WO 03/003949 | 1/2003 |
| WO | WO 03/011195 | 2/2003 |
| WO | WO 03/015851 | 11/2003 |
| WO | WO 2004/019811 | 3/2004 |
| WO | WO 2004/023980 | 3/2004 |
| WO | WO 2004/041126 | 5/2004 |
| WO | WO 2004/045383 | 6/2004 |
| WO | WO 2004/047681 | 6/2004 |
| WO | WO 2005/013860 | 2/2005 |
| WO | WO 2005/027736 | 3/2005 |
| WO | WO 2005/039452 | 5/2005 |

OTHER PUBLICATIONS

Bonhoeffer, "Percutaneous insertion of the pulmonary valve," Journal of American College of Cardiology Foundation, (2002) 39(10):1664-1669.

Safi et al., "Repeat replacement of aortic valve bioprosthesis," Ann. Thorac.Surg., (1995), 59:1217-1219.

* cited by examiner

PROSTHETIC CARDIAC VALVES AND SYSTEMS AND METHODS FOR IMPLANTING THEREOF

RELATED APPLICATIONS

This application is a continuation of U.S. patent application Ser. No. 11/003,693, filed Dec. 3, 2004 now U.S. Pat. No. 7,186,265 which claims the benefit of U.S. Provisional Application No. 60/528,620, filed Dec. 10, 2003. The entire contents of that provisional application are herein incorporated by reference.

FIELD OF THE INVENTION

The invention relates to prosthetic cardiac valves and systems and methods for implanting them in a subject.

BACKGROUND OF THE INVENTION

The human heart has four valves that control the direction of blood flow through the four chambers of the heart. On the left or systemic side of the heart are the mitral valve, located between the left atrium and the left ventricle, and the aortic valve, located between the left ventricle and the aorta. These two valves direct oxygenated blood coming from the lungs, through the left side of the heart, into the aorta for distribution to the body. On the right or pulmonary side of the heart are the tricuspid valve, located between the right atrium and the right ventricle, and the pulmonary valve, located between the right ventricle and the pulmonary artery. These two valves direct de-oxygenated blood coming from the body, through the right side of the heart, into the pulmonary artery for distribution to the lungs, where it again becomes re-oxygenated to begin the circuit anew. With relaxation and expansion of the ventricles (diastole), the mitral and tricuspid valves open, while the aortic and pulmonary valves close. When the ventricles contract (systole), the mitral and tricuspid valves close and the aortic and pulmonary valves open.

Each of the four valves consists of moveable "leaflets" that are designed to open and close in response to differential pressures on either side of the valve. The mitral and tricuspid valves are referred to as "atrioventricular valves" as they are situated between an atrium and ventricle on each side of the heart. The mitral valve has two leaflets and the tricuspid valve has three. The aortic and pulmonary valves are referred to as "semilunar valves" because of the unique appearance of their leaflets, which are more aptly termed "cusps" and are shaped somewhat like a half-moon. The aortic and pulmonary valves each have three cusps.

Heart valve disease is a widespread condition in which one or more of the valves of the heart fail to function properly. Diseased heart valves may be categorized as either stenotic, wherein the valve does not open sufficiently to allow adequate forward flow of blood through the valve, or incompetent or insufficient, wherein the valve does not close completely, causing excessive backward flow of blood through the valve into the prior chamber when the valve is closed. Both of these conditions increase the workload on the heart and, if left untreated, can lead to debilitating symptoms including congestive heart failure, permanent heart damage and ultimately death. Dysfunction of the left-sided valves—the aortic and mitral valves—is typically more serious since the left ventricle is the primary pumping chamber of the heart.

Dysfunctional valves can either be repaired, with preservation of the patient's own valve, or replaced with some type of mechanical or biologic valve substitute. Since all valve prostheses have some disadvantages (e.g., need for lifelong treatment with blood thinners, risk of clot formation and limited durability), valve repair, when possible, is usually preferable to replacement of the valve. Many dysfunctional valves, however, are diseased beyond the point of repair. In addition, valve repair is usually more technically demanding and only a minority of heart surgeons is capable of performing complex valve repairs. The appropriate treatment depends on the specific valve involved, the specific disease/dysfunction and the experience of the surgeon.

The aortic valve, and less frequently the pulmonary valve, are more prone to stenosis, which typically involves the buildup of calcified material on the valve leaflets, causing them to thicken and impairing their ability to fully open to permit adequate forward blood flow. Most diseased aortic and pulmonic valves are replaced rather than repaired because their function can be easily simulated with a replacement prosthesis and because the typical types of damage to these valves is not easily repairable.

The mitral valve, and less commonly the tricuspid valve, are more commonly affected by leaflet prolapse. While regurgitant mitral valves can be repaired, many are replaced due to the complexities of surgically correcting the underlying redundant valve segments, ruptured chordae, and papillary muscle malposition.

The most common treatment for stenotic valves, particularly aortic valves, is the surgical replacement of the diseased valve. If a heart valve must be replaced, the choice of a particular type of prosthesis (i.e., artificial valve) depends on factors such as the location of the valve, the age and other specifics of the patient, and the surgeon's experiences and preferences. Two major types of prosthetic or replacement heart valves exist: mechanical prostheses and biologic prostheses.

Mechanical prostheses are generally formed entirely of artificial material, such as carbon fiber, titanium, Dacron™ and teflon. There are currently three widely used types of mechanical prostheses: the Starr-Edwards ball-in-cage valve, the Medtronic-Hall tilting disc valve, and the St. Jude bi-leaflet valve. Caged ball valves usually are made with a ball made of a silicone rubber, e.g., SILASTIC™, inside a titanium cage, while bi-leaflet and tilting disk valves are made of various combinations of pyrolytic carbon and titanium. All of these valves are attached to a cloth material sewing ring or mounting cuff so that the valve prosthesis can be sutured to the patient's native tissue to hold the artificial valve in place postoperatively. All of these mechanical valves can be used to replace any of the heart's four valves.

Although mechanical valves have proven to be extremely durable, they all require life-long anticoagulation with blood thinners to prevent clot formation on the valve surfaces. If such blood clots form on the valve, they may preclude the valve from opening or closing correctly or, more importantly, the blood clots may disengage from the valve and embolize to the brain, causing a stroke. The anticoagulant drugs that are necessary to prevent this are expensive and potentially dangerous in that they may cause abnormal bleeding or other side effects. Mechanical valves have the further disadvantage in that the mounting cuffs or sewing rings occupy space, narrowing the effective orifice area of the valve and reducing cardiac output.

The second major type of prosthetic or replacement heart valve is a biologic or tissue valve. These valves include allografts or homografts (usually a valve transplanted from a donor cadaver), autologous grafts (constructed from non-valvular tissue (e.g. pericardium) or from another cardiac valve from the patient himself) and xenografts (animal heart valves typically harvested from cows and pigs). Commercially available biologic tissue valves include the Carpentier-Edwards Porcine Valve, the Hancock Porcine Valve, and the Carpentier-Edwards Pericardial Valve. Recently, there has been an increasing effort to develop synthetic biologically compatible materials to substitute for these natural tissues.

Tissue valves have the advantage of a lower incidence of blood clotting (thrombosis). Hence patients receiving such a valve, unlike those receiving a mechanical valve, do not require prolonged anticoagulation therapy with the potential clinical complications, expense, and patient inconvenience. The major disadvantage of tissue valves is that they lack the long-term durability of mechanical valves. Tissue valves have a significant failure rate, usually appearing at approximately 8 years following implantation, although preliminary results with the new commercial pericardial valves suggest that they may last longer. One cause of these failures is believed to be the chemical treatment of the animal tissue that prevents it from being antigenic to the patient.

Bioprosthetic or tissue valves are provided in stented or unstented forms. A stented valve includes a permanent, rigid frame for supporting the valve, including the commissures, during and after implantation. The frames can take the form of a plastic, wire or other metal framework encased within a flexible fabric covering. Unstented valves do not have built-in commissure supports.

While the stented tissue valves guarantee alignment of the commissures, they cause very high stresses on the commissures when the valve cusps move between open and closed positions. Additionally, the frames or stents can take up valuable space inside the aorta such that there is a narrowing at the site of valve implantation. As with mechanical valves, the frame includes artificial materials which can increase the risk of new infection or perpetuate an existing infection.

In many situations, biologic replacement heart valves are preferred in the unstented form due to the drawbacks mentioned above. Such valves are more resistant to infection when implanted free of any foreign material attachments, such as stents or frames. Despite the known advantages of using biologic prosthetic heart valves without artificial supporting devices such as permanent stents or frames, relatively few surgeons employ this surgical technique due to its high level of difficulty. When unsupported or unstented by a frame or stent, biologic replacement heart valves are flimsy and overly flexible such that the commissures of the heart valve do not support themselves in the proper orientation for implantation. For these reasons, it is very difficult to secure the commissures properly into place. In this regard, the surgeon must generally suture the individual commissures of the heart valve in the exact proper orientation to allow the valve to fully and properly function.

Regardless of the type of valve used, a valve replacement procedure first involves excising the natural valve from the heart. The natural annulus is then sized with a sizing instrument. After the size has been determined, a valve is then selected for a proper fit. Proper sizing is important as an oversized replacement valve can cause coronary ostial impingement or tearing of the natural annulus. On the other hand, an undersized valve will reduce flow volume and cardiac output. Next, sutures are placed in the natural valve annulus. Usually, a plurality of very long sutures are applied to the annulus, and are carefully laid out to extend through the incision in patient's chest to points outside the incision. Various suture techniques may be used, including simple interrupted, interrupted vertical mattress, interrupted horizontal mattress with or without pledgets, or continuous, depending on the anatomical structure of the valve being replaced, the type of replacement valve being used, and the particular patient's anatomy. Regardless of the specific suturing technique employed, suture placement within the native valve annulus is crucial to the outcome of the valve replacement procedure, requiring accurate and flawless suturing. After placement in the natural valve annulus, working outside of the chest, the same sutures are placed through the valve's mounting cuff or sewing ring, which is provided fixed to the valve itself. The individual sutures are specifically placed on the valve to provide the proper orientation of the valve with respect to the valve annulus. The valve and sewing ring are then "parachuted" or slid down the sutures and seated within the native valve annulus with the proper valve orientation maintained. The sutures anchoring the cuff of the prosthesis to the host tissue are then tied off and the excess suture length trimmed.

While suturing of replacement valves has long been the accepted technique in implanting prosthetic valves, this technique is replete with shortcomings. Suturing of a valve is a very complex procedure, requiring the utmost care and accuracy. As such, improperly suturing a replacement valve is not inconsequential. Correcting inadequately placed valves may require complete removal of the valve (i.e., by cutting the sutures holding the valve) and reseating the valve as described above. Repetition of the suturing process causes excessive perforation of the native valve annulus subjecting it to risk of tearing and may effect the functioning of the replacement valve once permanently placed. This risk also presents itself in subsequent surgeries performed to replace a prosthetic valve suffering from excessive wear or mechanical failure. The sutures holding the prosthetic device in place must be removed and a new device inserted and resutured to the surrounding tissue. After a number of replacements, the tissue surrounding the valve becomes perforated and scarred making attachment of each new replacement valve progressively more difficult for the surgeon and riskier for the patient.

In addition to the complexity of valve suturing, conventional heart valve replacement surgery can be very invasive, involving access to the patient's heart through a large incision in the chest, such as a median sternotomy or a thoracotomy. Since conventional valve replacement procedures involve work inside the heart chambers, a heart lung machine is required. During the operation, while the patient is "on the pump," the heart is isolated from the rest of the body by clamping the aorta and stopped (cardioplegic arrest) through the use of a high potassium solution. Although most patients tolerate limited periods of cardiopulmonary bypass and cardiac arrest, these maneuvers are known to adversely affect all organ systems. The most common complications of cardiopulmonary bypass and cardiac arrest are stroke, myocardial "stunning" or damage, respiratory failure, kidney failure, bleeding and generalized inflammation. If severe, these complications can lead to permanent disability or death. The risk of these complications is directly related to the amount of time the patient is on the heart-lung machine ("pump time") and the amount of time the heart is stopped ("cross-clamp time").

The complex suturing of the prosthetic valve within the valve annulus and the subsequent knot tying involved in valve replacement procedures, as discussed above, is very time consuming, requiring a significant amount of pump time. Because the success of valve replacement can only be determined when the heart is beating, the heart must be closed up and the patient taken off the heart lung machine before verification can be made. If the results are determined to be inadequate, the patient must then be put back on cardiopulmonary bypass and the heart stopped once again.

Recently, a great amount of research has been done to reduce the trauma and risk associated with conventional open-heart valve replacement surgery. A variety of minimally invasive valve repair procedures have been developed whereby the procedure is performed through small incisions with or without videoscopic assistance and, more recently, with robotic assistance. However, the time involved in these minimally invasive procedures is often greater than with conventional valve replacement procedures as the suturing process must now be performed with limited access to the valve and, thus, limited dexterity even in the hands of experienced surgeons.

Other technologies are being developed in the area of cardiac valve replacement with the hope of overcoming the disadvantages of suturing by simplifying the valve attachment procedure and reducing the time necessary to complete such procedure. These proposed technologies include stapling and fastening devices that deploy one or more staples or fasteners at the valve attachment site in a single action. Examples of such technologies are disclosed in U.S. Pat. Nos. 5,370,685, 5,716,370, 6,042,607, 6,059,827, 6,197,054, and 6,402,780. Although stapling and fastening may save time, great precision and accuracy are required to ensure proper placement and alignment of the replacement valve prior to placement of the staples/fasteners. An improperly placed staple or fastener can be very difficult to remove at the risk of tearing or damaging the tissue at the valve site. Another sutureless valve replacement technology which has been disclosed but remains to be clinically proven is that of employing thermal energy, such as radio frequency energy, to shrink the natural valve annulus around a prosthetic valve placed within it. An example of this technology is disclosed in U.S. Pat. No. 6,355,030.

Thus, it is desirable to provide a prosthetic cardiac valve system, the implant of which requires a minimum of amount suturing and preferably no suturing in order to decrease the amount of time the patient's heart would need to be stopped and bypassed with a heart-lung machine. It would be additionally advantageous if such cardiac valve could be removed or its position adjusted once implanted, either at the time of the original implant procedure or in a subsequent operation. It would be additionally desirable if such prosthetic cardiac valve could be implanted without the need for cardiopulmonary bypass and cardioplegic arrest. Still yet, a further advantage would be to provide a prosthetic valve that could be implanted by means of percutaneous or endovascular approaches.

SUMMARY OF THE INVENTION

The present invention includes prosthetic cardiac valves and valve replacement systems, and methods of implanting the prosthetic valves. Magnets are employed within one or more components of the valve systems to facilitate anchoring of the prosthetic valve at a target implant site, delivery of the prosthetic valve to the target implant site or both.

In certain embodiments, the valve replacement systems include a valve mechanism and a fixation mechanism for anchoring or retaining the valve mechanism at a selected target implant site. The valve and fixation mechanisms are provided separately and are coupled together by magnetic coupling means upon implantation where one or more magnets are provided on each of the valve and fixation mechanisms. In certain of these embodiments, the magnetic coupling means not only function to couple the valve mechanism to the fixation mechanism, but further function to anchor the operatively coupled mechanisms within the implant site. In other variations of the invention, the fixation mechanism is itself anchored or affixed to the implant site by ancillary means such as sutures, pins, barbs or the like. In still other embodiments of the present invention, the valve mechanism is self-anchoring and does not require a separate fixation mechanism.

Some of the embodiments are suitable for either surgical, minimally invasive or endovascular delivery approaches. At least a portion of the valve mechanism and/or fixation mechanism is flexible so as to be compressible or collapsible or foldable to provide a low-profile state for minimally invasive and endovascular delivery, and which is expandable for deployment at an implant site. In certain variations of these, the valve mechanism is held together in the collapsed or folded condition by magnetic means which means may also facilitate anchoring of the valve mechanism when deployed at the implant site. Still other variations provide a stent mechanism to facilitate delivery and deployment of the fixation mechanism.

An object of the present invention is to simplify cardiac valve replacement procedures and reduce the time to perform such procedures.

Another object of the invention is to minimize the amount of suturing required to implant a prosthetic valve and, preferably, to eliminate the need for suturing altogether.

Yet another object of the present invention is to provide a valve implantation system that enables the minimally invasive or percutaneous delivery of a replacement valve to the target site.

Another object of the present invention is to provide a valve implantation system that does not require the use of cardiopulmonary bypass and/or cardioplegic arrest.

Yet another object of the presentation is to provide a valve implantation system that minimizes the amount of space at the natural valve orifice that the system occupies.

A feature of the present invention is a valve implantation system that requires minimal suturing.

Another feature of the present invention is a sutureless valve.

Another feature of the present invention is a prosthetic valve which is held in an implanted position substantially by or solely by magnetic force.

Another feature of the present invention is a valve implantation system that does not require penetrating or piercing the tissue at the implant site.

Another feature of the present invention is a collapsible valve mechanism

Another feature of the present invention is a valve implantation system that can be delivered to an implant site through a catheter.

Another feature of the present invention is a valve implantation system that can be delivered to an implant site through a port in the thoracic cavity.

A feature of the present invention is a valve implantation system in which the valve and fixation mechanism (mounting or docking ring) are separable structures that may be readily engaged and disengaged.

Another feature of the present invention is a valve implantation system in which the valve and fixation mechanism are separately deliverable to the implant site.

Another feature of the present invention is a valve implantation system wherein a valve can be positioned at a target implant site, repositioned or removed and reinserted contemporaneously during a single procedure.

Still another feature of the present invention is a valve implantation system wherein the valve can be implanted at a target implant site and subsequently removed and replaced in a later procedure.

These and other features and advantages of the invention will become apparent to those skilled in the art upon reading and understanding the following detailed description and accompanying drawings.

BRIEF DESCRIPTION OF THE DRAWINGS

The following drawings are provided and referred to throughout the following description, wherein like reference numbers refer to like components throughout the drawings.

DETAILED DESCRIPTION OF THE INVENTION

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

For purposes of the present invention, references to positional aspects of the present invention will be defined relative to the directional flow vector of blood flow through the implantable device, i.e., one or more of an implantable valve, an implantable docking port, a stent, etc. Thus, the term "proximal" is intended to mean the inflow or upstream flow side of the device, while "distal" is intended to mean the outflow or downstream flow side of the device. With respect to the valve implantation instrumentation, including the catheter delivery system, described herein, the term "proximal" is intended to mean toward the operator end of the instrument or catheter, while the term "distal" is intended to mean toward the terminal or working end of the instrument or catheter.

The present invention includes implantable cardiac valve systems and devices and methods of implanting and using the subject systems. The implantable devices include prosthetic replacement cardiac valves, valve docking ports or rings, stent devices and the like. The implantable devices may be provided in kits with or without instrumentation for the surgical, minimally invasive or percutaneous or endovascular delivery and deployment of the implantable devices.

The detailed description set forth below in connection with the appended drawings is intended merely as a description of the presently preferred embodiments of the invention, and is not intended to represent or limit the form in which the present invention can be constructed or used. It is to be understood that the same or equivalent functions and sequences may be accomplished by different embodiments that are also intended to be encompassed within the spirit and scope of the invention. For example, the present invention is particularly suitable for replacing aortic valves and, thus, is primarily described in the context of aortic valve replacement for purposes of example only. Such exemplary application of the present invention is not intended to limit the invention in any way as the present invention is suitable for the replacement of other cardiac valves or for implantation into any other location within the vasculature or within an organ of any subject. Moreover, while an exemplary embodiment of the present invention is illustrated herein as a cardiovascular valve system for use in connection with the heart, the present invention is contemplated for use as a valve system with other organs or anatomical structures.

The prosthetic valves of the present invention are not limited to a particular construction or to particular materials. The valves may have any suitable configuration and be made of any suitable materials depending on the surgeon's preference, the particular valve being replaced, the specific needs and condition of the patient, and the type of approach being used for delivery of the valve, i.e., surgical (i.e., through a sternotomy or thoracotomy), minimally invasive (e.g., port access), endovascular (i.e., catheter-based) or a combination of the above.

If an endovascular implantation approach is preferred, a highly flexible valve prosthesis is necessary, in which case, the leaflets and annulus structures, as well as the mounting ring or cuff structure (if applicable), are preferably formed of flexible material which may be a natural tissue or a biologically compatible synthetic material. As the annulus of the prosthetic valve as well as the mounting structure may require some rigidity, a shaped memory material, such as Nitinol or other alloy material, which is collapsible and/or expandable yet able to provide radial strength and integrity to the valve structure. Another material which is flexible when placed under stress but which provides a significant amount of rigidity when unstressed is silicone. As will be understood from the following description of the invention, such properties make silicone or the like very suitable and highly advantageous for use with the valve mechanisms of the present invention. The magnetic components, which are described below in greater detail, may also be constructed so as to have some flexibility.

If a surgical implantation approach is preferred, the surgeon has the option to use a prosthetic valve made entirely of rigid materials or entirely flexible materials or a combination of both. For example, a mechanical heart valve may be manufactured with rigid occluders or leaflets that pivot to open and close the valve, or flexible leaflets that flex to open and close the valve.

Whether rigid, flexible or both, the prosthetic valves of the present invention may be constructed from natural materials, e.g., human, bovine or porcine valves or pericardial tissue, or synthetic materials, e.g., metals, including super elastic metals such as Nickel Titanium and malleable metals such as stainless steel, ceramics, carbon materials, such as graphite, polymers, such as silicone, polyester and polytetrafluoroethylene (PTFE), or combinations of natural and synthetic materials.

In addition to material considerations, the structure of the replacement valve is also dictated by the type of valve being replaced. For example, replacement aortic valves are most preferably trifoliate as they more closely mimic the action of the natural aortic valve, while replacement mitral valves are most preferably bi-leaflet. It should be noted that while only trifoliate and bi-leaflet valve mechanisms are illustrated and described in the context of this description, such illustration and description is not intended to be limiting.

The prosthetic valves of the present invention, when in an expanded or deployed state, have sizes and dimensions which are comparable to conventional replacement valves. The size and various dimensions of the valves and docking mechanisms of the present invention when in a collapsed or low-profile will vary depending on the size of the conduit through which it is delivered. For example, typical catheter sizes for cardiovascular applications range from about 15 Fr to about 15 Fr, but may be greater or smaller depending on the specific application. Typical thoracic port or cannula diameters for port access applications in the thoracic cavity range from about 8 mm to about 12 mm, but may be greater or smaller depending on the specific application.

The prosthetic valve systems of the present invention, particularly the blood-contacting surfaces of the valve systems, may be coated or treated to promote better thrombogenecity and/or to improve flow there through. Some exemplary materials that may be used to coat or otherwise treat the replacement valves of the present invention include gold, platinum, titanium nitride, parylene, silicone, urethane, epoxy, Teflon and polypropylene.

From a review of the following description, it should be understood that the principles of the present invention can be applied to any prosthetic valve, regardless of the valve being replaced (aortic, mitral, tricuspid, pulmonic, etc.), the type of material being used (natural or synthetic or both), and the physical characteristics of the materials being used (flexible or rigid or both).

Figure 1:
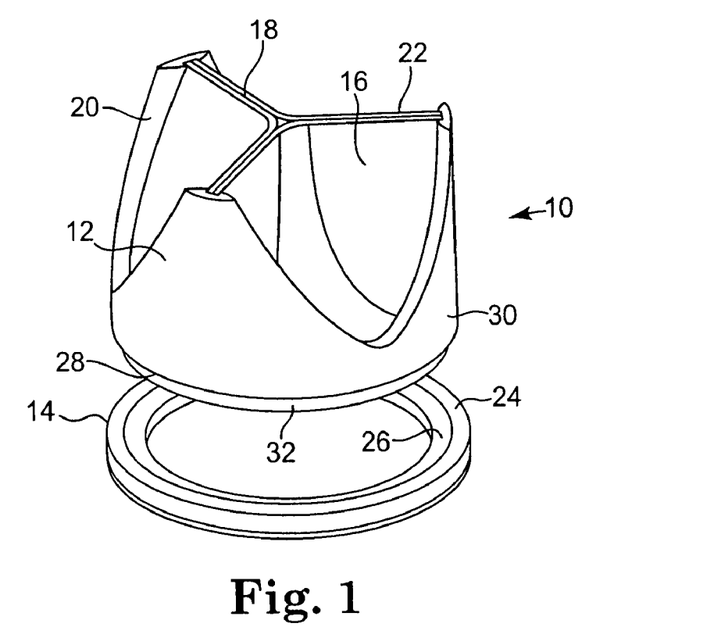
FIG. 1 is a perspective view of an embodiment of a prosthetic valve replacement system of the present invention including a prosthetic valve mechanism and an internal valve fixation or docking mechanism.

Referring to the drawings, wherein like reference numbers refer to like components throughout the drawings, FIG. 1 illustrates a prosthetic valve system 10 of the present invention having a valve mechanism 12 and a valve fixation or securing mechanism or docking port 14. Valve mechanism 12 has a trifoliate configuration having three leaflets or cusps 16 supported by commissure portions 20 extending from base or body 30. Each cusp 16 terminates at a free edge 18 at the outflow end 22 of valve mechanism 12. Fixation mechanism 14 is in the form of a docking ring or cuff and is designed to be internally seated within a natural valve annulus. It is sized (diametrically) to exert a radially compressive force against the natural annulus or the aortic wall (in the case aortic valve replacement) where such force is sufficient to maintain the fixation mechanism 14 in its operative position under normal conditions without exerting unnecessary force to the aortic wall. In certain embodiments, valve mechanism 12 may also have a diameter which provides a radially compressive force against the contact tissue structure; however, such is not necessary.

Docking ring 14 has an outer portion or perimeter region 24 and an inner portion or interior region 26. Outer portion 24 functions as a sewing ring or cuff and is made of cloth or other suitable material as known in the art through which sutures may be applied to operatively secure the ring within a native valve annulus. Inner portion 26 is at least in part formed of a magnetic material. The entirety of the inner portion 26 may be made exclusively of the magnetic material or, alternatively, may include one, two or more discrete sections of magnetic material. A corresponding magnetic material 28 is provided at the inflow end 32 of valve mechanism 12. As with the magnetic material 26 of docking port 14, magnetic material 28 may underlie the entirety of valve base 30 or be provided in a plurality of discrete sections.

Magnets 26 and 28 have polarities wherein a magnetic field between the two causes valve mechanism 12 and securing mechanism 14 to couple in a desired positional relationship with each other, collectively defining a securing or locking mechanism. Embodiments where one of or both the docking magnet 26 and the valve magnet 28 are continuous or complete, forming a ring, the polarities of the two magnets are always opposite. With such a configuration, any relative rotational alignment between the valve mechanism and the docking port may be provided (i.e., within 360°) and, as such, must be controlled or selected by the physician. In other embodiments, each of magnets 26 and 28 have a discontinuous or spaced apart configuration, i.e., each is comprised of one or more discrete magnetic segments or a plurality of magnetic segments, the polarities and resulting locking arrangements of which are best described below with respect to the embodiments of FIGS. 2A-C. In either embodiment, when operatively positioned within a native valve annulus, the two magnets 26 and 28 directly contact each other in a head-to-toe or a top-to-bottom arrangement and form a magnetic bond sufficient to provide a fluid-tight seal between the two and sufficient to maintain the seal during normal valve and cardiac motion.

Figure 2A:
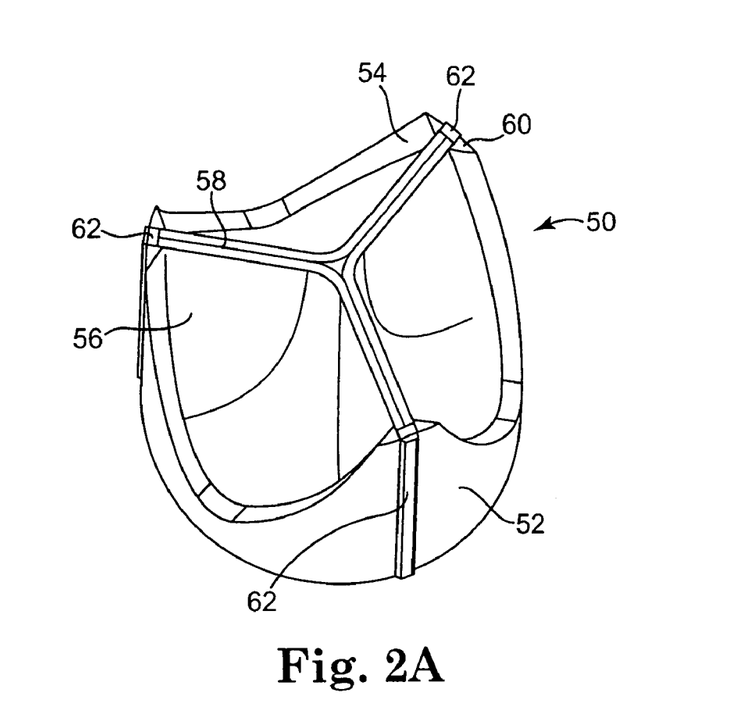
FIG. 2A is a perspective view of another embodiment of a prosthetic valve mechanism of the present invention.
Figure 2B:
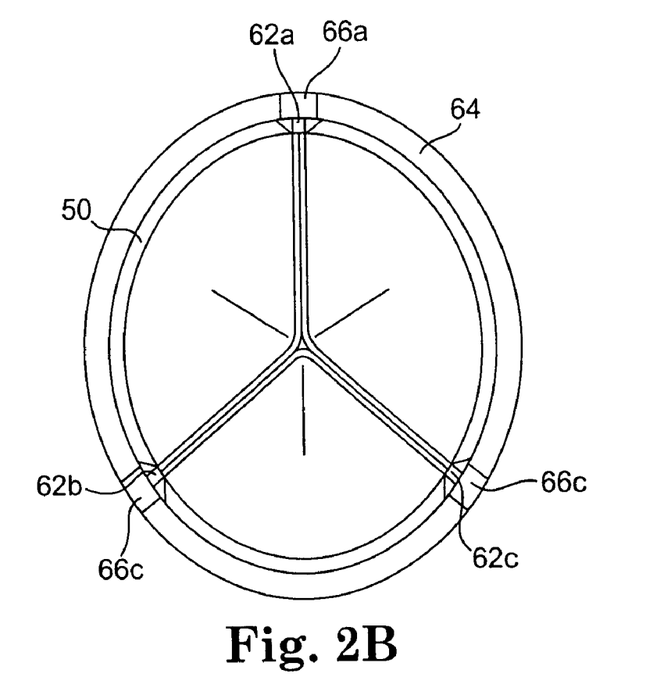
FIG. 2B is a top view if the valve mechanism of FIG. 2A operatively engaged with an external fixation or docking mechanism.
Figure 2C:
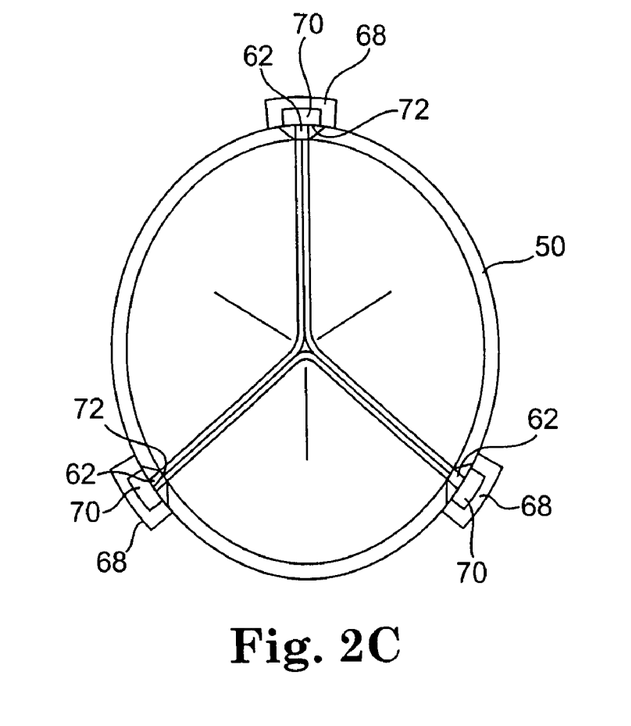
FIG. 2C is a top view if the valve mechanism of FIG. 2A operatively engaged with another embodiment of an external fixation or docking mechanism.

FIGS. 2A-C illustrate another prosthetic valve system of the present invention which includes a valve mechanism 50 having a construct and configuration similar to that of valve mechanism 12 of FIG. 1. Valve mechanism 50 includes a base or body 52 having three commissure portions 54 and three cusps 56 which merge at their free edges 58 at outflow end 60. On the outside surface of valve body 52, at each commissure 54, are magnetic components or inserts 62. While magnetic inserts 62 are shown parallel to the flow axis of the valve and extend the height of the respective commissure 54, magnetic inserts 62 may have any suitable location about the perimeter of valve body 52 and may have any suitable shape or size. Magnetic components 62 enable valve mechanism 50 to magnetically couple with a fixation or securing mechanism having corresponding magnetic components.

Unlike the internal docking port 14 of valve system 10 of FIG. 1, the docking mechanisms suitable for use with valve mechanism 50 are designed to be used outside or about the outer wall of a native valve annulus, wherein when valve mechanism 50 and the fixation mechanism are operatively placed, the native valve annulus and/or adjacent tissue is sandwiched in between the two (not shown). The fixation mechanism may take the form of a complete or partial ring such as docking ring 64 of FIG. 2B having spaced apart magnetic components 66. Preferably there is a one-to-one relationship between the magnetic components 62 of valve mechanism 50 and the magnetic components 66 of docking port 64. Docking ring 64 has an internal diameter sufficient to encircle the outer diameter of valve mechanism 50 thereby providing a concentric coupling arrangement. While the majority of the force holding docking ring 64 and valve mechanism 50 in operative engagement may be attributed to the magnetic force between their magnetic components, docking ring 64 provides a compressive force which further contributes to maintaining the operative position of valve mechanism 50.

Alternatively, the fixation mechanism may include a plurality of individual magnetic components 68 as shown in FIG. 2C which may be placed in a spaced apart arrangement about the perimeter of valve mechanism 50 wherein a magnetic component 68 is rotationally aligned with a corresponding magnetic component 62. Preferably there is a one-to-one relationship between magnetic components 62 of valve mechanism 50 and magnetic components 68. Magnetic components 68 may be made entirely of magnetic material or may have a non-magnetic support structure which holds or contains a magnetic segment 70 exposed on at least the surface 72 of the support structure that is intended to face valve mechanism 50. The valve facing surface 72 preferably has a radius of curvature that corresponds to the radius of curvature of the circumference of valve mechanism 50 as well as to the outer wall of the tissue structure in which the valve is placed, e.g., the aorta. Because magnetic components 68 do not encircle the aortic wall, very little of the force holding valve mechanism 50 in place is due to compression. As such, the force exerted by magnets 68 may be required to be greater than the magnetic force of magnets 66 of docking ring 64.

While the above-described prosthetic valve embodiments may be implantable by means of minimally invasive approaches, e.g., by port access (via thoracic ports), they may also be implantable by means of endovascular approaches whereby the valve and docking mechanism are delivered via a catheter provided that the valve and docking components are made of a material or materials that are flexible enough to enable catheter-based delivery to the implant site. In addition to the use of flexible materials, certain structural features may be incorporated into the components to facilitate percutaneous or catheter-based delivery of the devices.

Figure 3A:
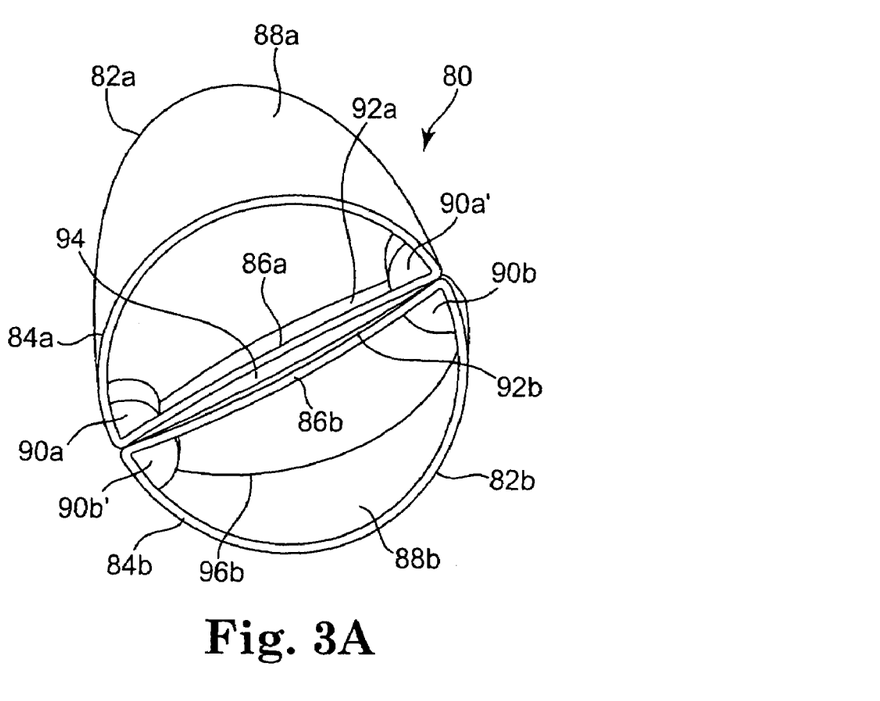
FIG. 3A is a perspective view of another embodiment of a prosthetic valve mechanism of the present invention particularly suited for minimally invasive or endovascular implantation approaches.
Figure 3B:
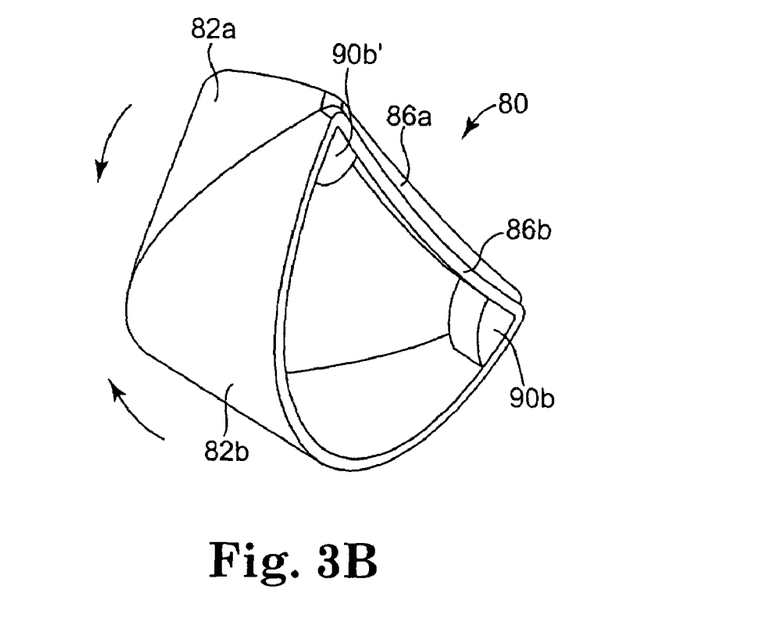
FIG. 3B is a side view of the valve mechanism of FIG. 3A in a compressed or low-profile configuration.
Figure 3C:
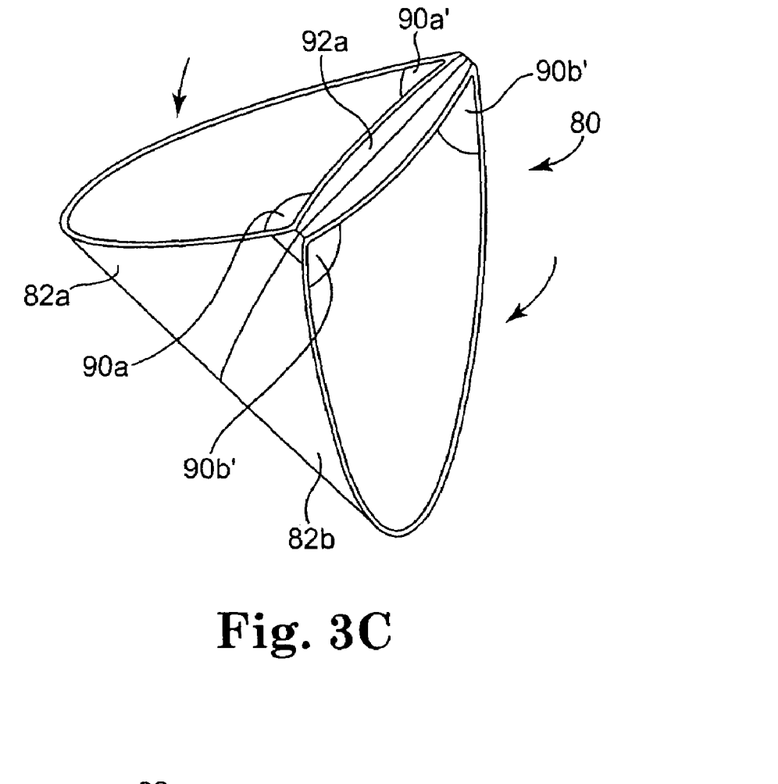
FIG. 3C is a side view of one piece or half of the valve mechanism of FIG. 3A in a compressed or low-profile configuration.

FIGS. 3A-3D illustrate another prosthetic valve mechanism 80 which lends itself to percutaneous delivery. FIG. 3A illustrates a bi-leaflet valve mechanism 80 in its operative, deployed condition while FIGS. 3B and 3C illustrate valve mechanism 80 in two possible collapsed, compressed or low-profile conditions making it suitable for delivery through a catheter or a narrow port. Valve mechanism 80 is formed by two pieces 82a, 82b with identical structures, each defining half of the valve's structure or body which supports a single leaflet 92a, 92b. Each half 82a, 82b of the valve body defines a cylindrical wall 88a, 88b having a sloped edge 96a, 96b which tapers distally toward the outflow end of the valve. The inflow or proximal end 84a, 84b of each piece or half 82a, 82b has a substantially semicircular or "D" shaped cross-section or flow path. The "straight" edge or secant 86a, 86b of the semi-circular inflow end is slightly concave thereby providing an inlet gap 94 through which blood flow enters. In the context of aortic valve function, as pressure builds within the left ventricle, gap 94 is caused to expand slightly allowing blood to pass through. Positioned within each corner of each piece 82a, 82b, is a magnet wherein each piece has a pair of magnets 90a, 90b which are oppositely polarized, i.e., magnets 90a and 90b are of one polarity and magnets 90a' and 90b' are of the opposite polarity.

Such an arrangement of magnets enables several possible configurations. First, when the two pieces are caused to face each other, as illustrated in FIG. 3A, the arrangement of magnets causes the two pieces to magnetically couple or engage along their respective straight edges or secants 86a, 86b. As coupled, the assembled valve mechanism 80 is operative as a one-way valve. Although the two pieces remain magnetically engaged, they are nonetheless hinged about their straight edges 86a, 86b. As such, the outflow ends of the pieces 82a and 82b may be compressed together or inwardly rotated (as illustrated by the arrows in FIG. 3B) such that their sloped edges 92a and 92b contact each other thereby forming a quadrangle or diamond-shaped structure, as illustrated in FIG. 3B. Alternatively, the outflow ends may be further separated from each other or outwardly rotated (as illustrated by the arrows in FIG. 3C) such that the semicircular edges 84a and 84b of the inflow ends of the valve contact each other thereby forming a triangular structure, as illustrated in FIG. 3C. With either of these collapsed or compressed configurations, the profile of the valve mechanism is reduced from its operative or deployed profile, thereby allowing it to be delivered and implanted by less invasive means, e.g., via a catheter or a cannula. Upon exiting the catheter or other delivery conduit, the two pieces 82a and 82b are expanded apart into their operative positions within the native valve site. While a two-piece valve mechanism has been illustrated and described, those skilled in the art will appreciate that a valve mechanism having more than two pieces, e.g., three or more, wherein the cross-sectional configuration of each piece is pie-shaped, may also be provided in accordance with the principles of the present invention.

Figure 3D:
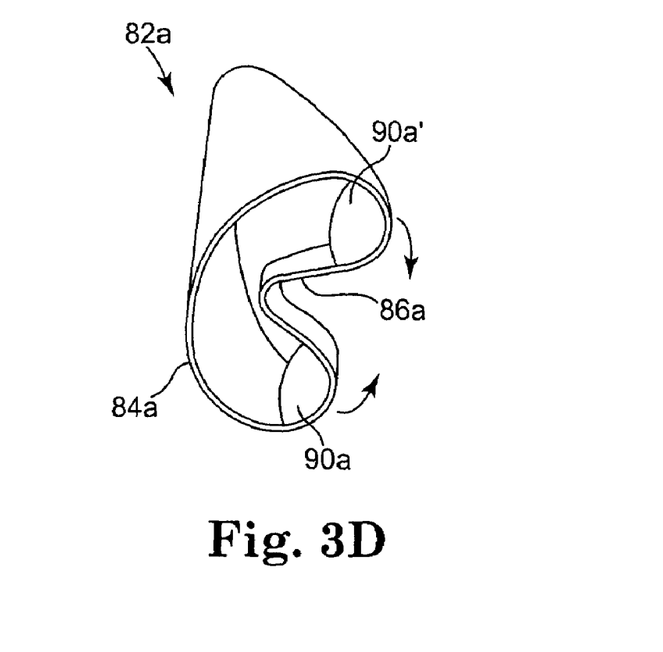
FIG. 3D is a side view of one piece or half of the valve mechanism of FIG. 3A in an alternate compressed or low-profile configuration.

With the valve body and valve leaflets made of a flexible material, such as silicone or the like, the above-described magnet arrangement provides another possible configuration. Specifically, each piece 82a, 82b may be individually folded whereby its straight or inlet edge 86a, 86b is compressed inwardly (as illustrated by the arrows in FIG. 3D) such that its magnets, which are oppositely polarized, cause the corners of the semicircular valve structure to become magnetically engaged, as illustrated in FIG. 3D. The profile of piece 82a, 82b which has been individually collapsed is substantially smaller than the profiles of the conjoined pieces as illustrated in FIGS. 3B and 3C. This very low profile enables the valve pieces to be delivered through an even narrower delivery conduit, either consecutively through a single catheter lumen or separately through two separate catheters or through a double lumen catheter. With the latter approach, while the two pieces are delivered separately, i.e., disengaged from each other, they may be deployed either simultaneously or consecutively.

In certain embodiments of the prosthetic valve of the present invention, such as the embodiment of FIG. 3, a fixation mechanism in not necessary or otherwise not used as the diameter of the valve mechanism in an expanded state is sufficiently large to cause the cylindrical walls of the valve to outwardly impinge upon and create a compression fit with the tissue surrounding the implant, e.g., aortic wall.

Figure 4A:
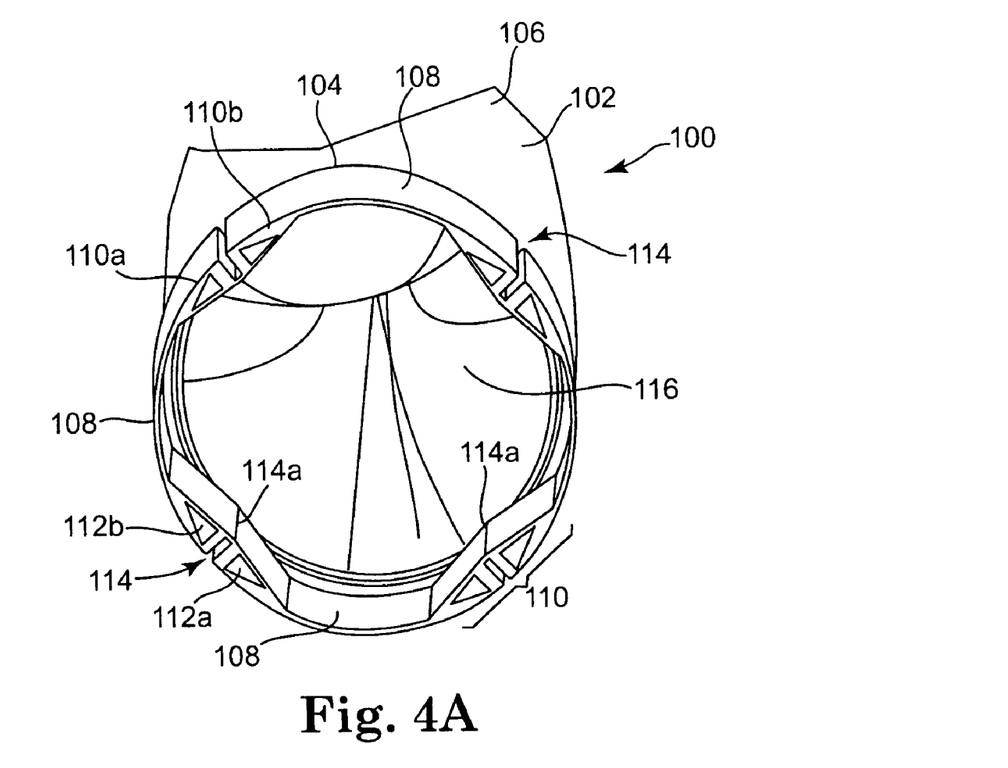
FIG. 4A is a perspective view of another embodiment of a prosthetic valve system of the present invention also suited for minimally invasive or endovascular implantation approaches.
Figure 4B:
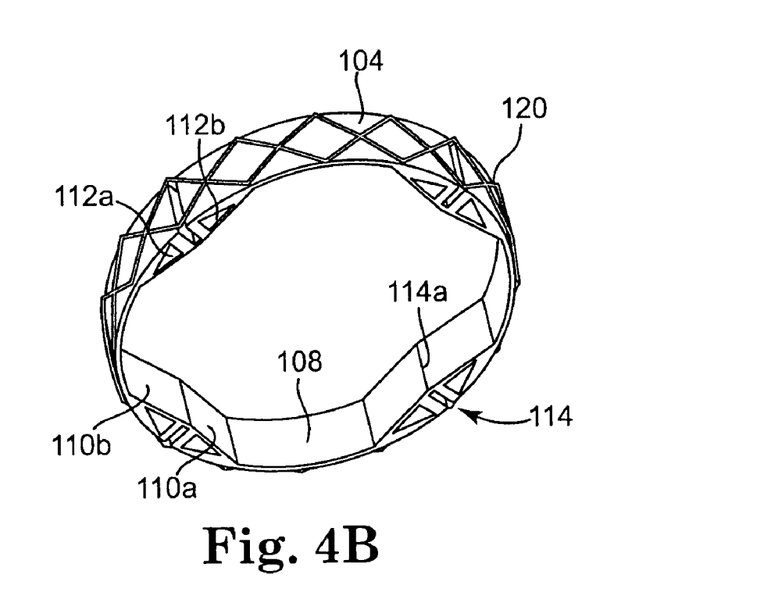
FIG. 4B is a perspective view of a valve fixation mechanism of the prosthetic valve system of FIG. 4A in an expanded or deployed configuration within a stent mechanism.
Figure 4C:
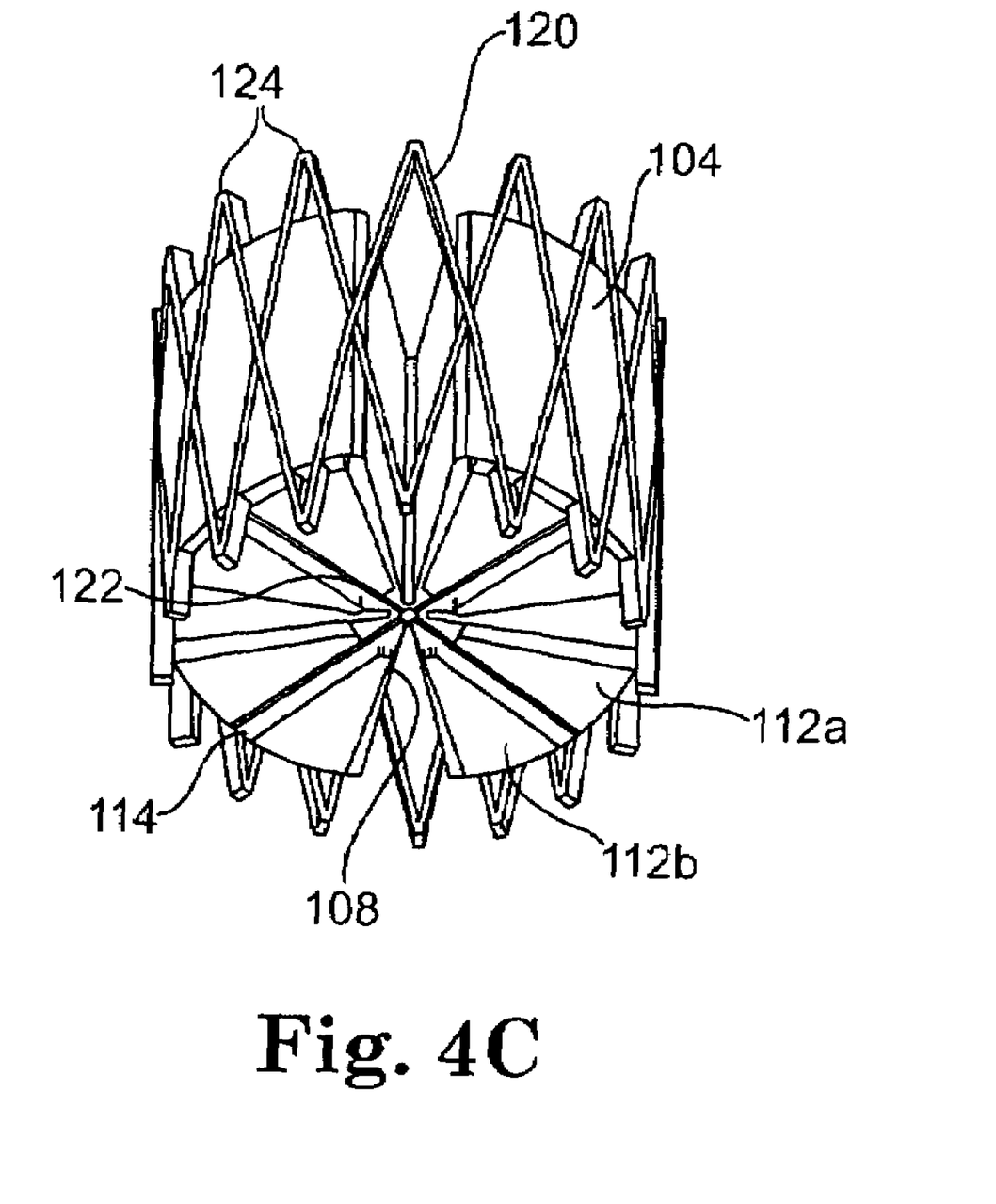
FIG. 4C is a perspective view of the valve fixation mechanism and stent mechanism of FIG. 4B in a compressed or low-profile configuration.

FIGS. 4A-4C illustrate another embodiment of a prosthetic valve system 100 of the present invention suitable for implantation by endovascular techniques. System 100 includes a valve mechanism 102 and a docking mechanism or port 104. Valve mechanism 102 includes a flexible valve body 106 and flexible leaflets 106 (any suitable number of leaflets may be employed). In certain embodiments, valve body 106 is constructed form silicone or the like and the leaflets 106 are formed from biological tissue. The inflow end of valve mechanism 102 is provided with a magnetic material (not shown) for magnetically coupling with docking port 104. The magnetic material may have any suitable configuration, e.g., a complete or partial ring, multiple magnetic segments, etc., as described infra.

Docking port 104 is in the form of a flexible and foldable thin-walled band which, in an unfolded or expanded condition has a circular configuration, as illustrated in FIGS. 4A and 4B, and in a folded or collapsed condition may have a petaled configuration, as illustrated in FIG. 4C; however, other folded or collapsed configurations may be employed, e.g., flattened and rolled. Preferably, band 104 is comprised of a compliant material, such as silicone, which allows it to be folded or collapsed in on itself at a plurality of points along its path. Band 104 has a plurality of magnetic sections 110 spaced apart, preferably evenly, about its structure, with intervening or intermediate sections 108. Each magnetic section 110 has a pair of magnets 112*a* and 112*b* imbedded within the wall of band 104, identified as wall sections 110*a* and 110*b*, respectively. A groove 114 within the external wall of band 104 extends between each pair of magnets to define a hinge joint or living hinge 114*a*. Magnets 112*a* and 112*b* are preferably oppositely polarized and, as such, may act to close groove 114 and provide a fluid-tight seal between the outer surface of band 104 and stent 120 when operatively deployed at an implant site. Magnets 112*a* and 112*b* are illustrated as having a triangular configuration, such as an isosceles triangle (i.e., having a relatively short base and longer sides). The magnets are positioned relative to each other wherein their bases are facing each other. In an expanded configuration, the magnet shape and arrangement, while making band 104 thicker at wall sections 110*a* and 110*b*, provides docking port 104 with a smooth, low-profile internal or fluid contacting surface to minimize any turbulence in the blood flow and to maximize the orifice diameter through which blood flows. Additionally, the magnet shape and arrangement allows for a maximum reduction in the diameter of docking port 104 when the docking port is in a collapsed condition, thereby reducing the necessary diameter of the conduit through which the docking port is delivered.

The delivery of docking port 104 through a conduit having a luminal diameter smaller than its own expanded diameter is facilitated by use of a stent mechanism 120 which can be manipulated to expand docking port 104 as desired. Stent 120 may have any suitable strut configuration which causes stent 120 to radially expand when axially shortened and to radially constrict when axially lengthened. Prior to being loaded into a delivery catheter, stent 120 is positioned about the external diameter of docking ring 104. The combined structure is radially compressed or constricted which action causes the intermediate sections 108 to fold inward which in turn causes the respective magnetic sections 110*a* and 110*b* to spread apart from each other and flex outwardly at living joints 114. Once the combined structure is fully constricted, it is loaded within the delivery conduit and translated within the lumen to the distal end of the conduit which is positioned at the implant site. Upon exiting the delivery conduit, the combined structure is expanded and deployed within the implant site.

The means for activating deployment is in part dependent upon the material and construct of stent 120. For example, stent 120 may be made of a superelastic material, e.g., Nitinol, which enables the stent to be self-expanding upon release from a constricted condition. If stent 120 is made of plastically deformable material, such as stainless steel, tantalum or the like, the stent and fixation band 104 may be expanded by means of a balloon, as commonly employed for stent placement within coronary arteries. In either embodiment, the stent and fixation band are biased radially outward and provide a compression fit within the implant site. Fixation of the stent and band within the implant site may be further facilitated by providing barbs or pins on the stent which penetrate into the surrounding tissue.

For embodiments of valve mechanisms or fixation mechanisms in which each have a plurality of magnetized segments, the polarities of those segments on each mechanism may be the same or may differ from each other. For example, all of the magnetic segments of a valve mechanism may be positively polarized while all of the magnetic segments of the corresponding fixation mechanism may be negatively polarized. Such configuration provides the most flexibility in the relative rotational positions of the two mechanisms. In other embodiments, the particular polarities of the mechanisms may be selected to provide a very limited or only a single possible orientation between the two mechanisms. For example, in the embodiment of FIG. 2B in which valve mechanism 50 has three magnetic segments 62*a*, 62*b* and 62*c*, and docking ring 64 has three magnetic segments 66*a*, 66*b* and 66*c*, a possible magnetic coupling arrangement might be as follows: valve segments 62*a* and 62*b* have a positive polarity and valve segment 62*c* has a negative polarity; fixation segments 66*a* and 66*b* have a negative polarity and fixation segment 66*c* has a positive polarity. As such, the only possible alignment or magnetic coupling between valve mechanism 50 and docking ring 64 is where negatively polarized valve segment 62*c* aligns with positively polarized fixation segment 66*c*. The valve system is thus "keyed" to ensure a predetermined alignment between the valve mechanism and the docking mechanism. This arrangement ensures that the valve mechanism is properly aligned within the host site in order to provide optimum fit and performance of the replacement valve, provided however, that the docking mechanism is itself properly positioned about the tissue structure into which the valve mechanism is implanted. Alternatively, polarity indicators may be used on the magnets themselves to indicate their respective polarities. The indicator may take the form of any suitable writing, emblem, color, etc. For example, the indicator may simply comprise the printed letters "N" or "S".

Generally, the number of magnetic segments on the valve and fixation mechanism and their relative polarities dictate the number of possible rotational alignments between the mechanisms. This allows great flexibility in indexing or selecting the orientation of the valve mechanism relative to the fixation mechanism. In the context of a cardiac valve replacement procedures where a particular, and possibly an exact, orientation of the valve within the implant site is necessary (this may especially be the case in which a leaflet type valve mechanism is used, rather than a ball-in-cage mechanism), a valve replacement system having a greater number of possible valve-to-fixation orientations allows the physician to fine-tune the valve's placement. If, on the other hand, the available access to and visibility of the implant site allow a surgeon to very accurately seat a docking ring within a native valve annulus, it would not be necessary, and possibly disadvantageous, to provide more than a limited number and possibly more than one possible orientation between the valve and the fixation mechanism. In applications where precise valve orientation is not an issue, a single or very limited number of magnetic segments may be used on the valve mechanism.

The magnetic material used with the devices and systems is preferably a permanent magnetic, ferromagnetic, ferrimagnetic or electromagnetic material. Suitable magnetic materials include but are not limited to neodymium iron boron (NdFeB), samarium cobalt (SmCo) and alnico (aluminum nickel cobalt). NdFeB is currently preferred for its force characteristics. The amount of force necessary to provide and maintain a fluid tight seal between a valve mechanism and a docking port (in either a serial or concentric relationship) under typical conditions and subject to typical flow dynamics is likely to varying depending on the particular valve implantation site. For example, the magnetic force necessary for a prosthetic valve used to replace an aortic valve may be greater than that necessary for a mitral valve replacement due to the greater pressures under which the aortic valve functions.

The magnetic coupling means employed with the subject valve replacement systems advantageously allow adjustment and realignment of the valve mechanism once seated within the natural valve annulus. Moreover, the implanted prosthetic valves may be removed and themselves replaced in subsequent operations with the same ease with which they were originally implanted.

With embodiments of the valve replacement systems that employ an internal valve fixation mechanism (such as illustrated in FIGS. 1 and 4A-4C), the fixation mechanism is preferably implanted at the implantation site prior to implantation of the valve mechanism. With embodiments employing an external valve fixation mechanism (such as illustrated in FIGS. 2A-2C), it may be preferable to implant the valve mechanism prior to the fixation mechanism. In either case, the separate or independent implantation of the fixation mechanism and the valve mechanism allow for greater visibility of the implant site and greater flexibility in the manner in which the mechanisms are delivered, i.e., the profile of each of the two mechanisms alone is smaller than the profile of the mechanisms when coupled together. Further, with embodiments of the present invention which do not employ fixation mechanisms, the number of steps and time involved in the procedure is greatly reduced. Moreover, the independently implanted valve mechanism maximizes the available cross-section of the flow path through the valve orifice.

As mentioned above, the devise of the present invention may be implanted through surgical access, minimally invasive port access or by percutaneous access or by a combination thereof. If the aorta, for example is dissected to access the natural valve for removal of it and subsequent placement of the prosthetic valve, cardiopulmonary bypass and cardioplegic arrest of the heart are necessary. However, if using port access and/or endovascular instruments and techniques to perform the valve replacement, cardiopulmonary bypass and cardioplegic arrest may not be necessary. Delivery, deployment and fixation of the subject valve devices and systems, as well as the steps to remove a native valve, if necessary, may be performed with or without videoscopic or endoscopic assistance or intra-operative transesophageal echocardiogram (TEE).

For endovascular procedures, delivery catheters having configurations similar to those used on the art for stent placement and the like may be used to facilitate the delivery of all necessary tools and instrumentation to the implant site, including but not limited to tools for excising the native valve tissue and for implanting the subject fixation and valve mechanism. A combination of endovascular and port-access techniques may be employed, for example, to implant the valve replacement system of FIGS. 2A-2C wherein the flexible and compressible valve mechanism is delivered endovascularly through a catheter and the external fixation ring or components are delivered through a port or cannula through the chest.

The catheter delivery systems suitable for endovascular delivery of the subject prosthetic valves and fixation mechanisms may employ any one or more of a variety of mechanisms and apparatuses for collapsing the subject devices, translating them through the lumen of a catheter, e.g., guide wires, expanding or deploying them, e.g., stents and balloons, and seating them at the target site. Many such mechanisms are known in the field of catheters for use in cardiovascular applications. For example, the devices may be deployed by mechanical, thermal, hydraulic and electrolytic mechanisms or a combination thereof.

Also provided by the subject invention are kits for use in practicing the subject methods. The kits of the subject invention include at least one subject prosthetic valve device of the present invention. Certain kits may include several subject valve devices having varying sizes. Additionally, the kits may include certain accessories such as an annulus sizer, a valve holder, suturing devices and/or sutures (for use with embodiments employing docking rings that are to be sutured to the valve annulus), delivery conduits, e.g., catheters and/or cannulae. Finally, the kits may include instructions for using the subject devices in the replacement of cardiac valves. These instructions may be present on one or more of the packaging, a label insert, or containers present in the kits, and the like.

It is evident from the above description that the features of the subject prosthetic valve systems and methods overcome many of the disadvantages of prior prosthetic valves and in the area of valve replacement generally including, but not limited to, minimizing or eliminating the need or time for suturing and facilitating minimally invasive approaches to valve replacement. As such, the subject invention represents a significant contribution to the field of cardiac valve replacement.

While the present invention has been described with reference to the specific embodiments thereof, it should be understood by those skilled in the art that various changes may be made and equivalents may be substituted without departing from the true spirit and scope of the invention. In addition, many modifications may be made to adapt to a particular indication, material, and composition of matter, process, process step or steps, while achieving the objectives, spirit and scope of the present invention. All such modifications are intended to be within the scope of the claims appended hereto.

What is claimed is:

1. In combination, a delivery conduit and a prosthetic valve replacement system for implantation at a target site within a subject, said prosthetic valve replacement system comprising:
- a valve mechanism;
- a fixation mechanism for retaining said valve mechanism in a fixed position at said target site; and
- magnetic means comprising magnetic material for magnetically coupling said valve mechanism with said fixation mechanism,
- wherein said fixation mechanism is changeable from a collapsed condition with magnetic material folded radially inward from a coupling position to an expanded condition with the magnetic material positioned at the coupling position for coupling with the valve mechanism.

2. The combination of claim 1, wherein magnetic material is provided as magnetic elements provided at spaced locations along the fixation mechanism that in its expanded condition comprises an annular element.

3. The combination of claim 2, wherein a plurality of pairs of magnetic elements are provided with hinge lines between at least one pair of magnetic elements to permit folding of the fixation mechanism to the collapsed condition.

4. The combination of claim 1, further comprising a stent operatively connected with the fixation mechanism that expands radially as the stent is axially shortened.

5. The combination of claim 4, wherein the stent is self-expanding so that by releasing a constriction provided to the stent, the stent expands to change the fixation mechanism from the collapsed condition to the expanded condition.

6. The combination of claim 4, wherein the stent is deformable so that by expanding the fixation mechanism, the stent is also expanded to maintain the fixation mechanism in the expanded condition thereof.

7. In combination, a delivery conduit and a prosthetic valve replacement system for implantation at a target site within a subject, said prosthetic valve replacement system comprising:
- a valve mechanism;
- a fixation mechanism for retaining said valve mechanism in a fixed position at said target site; and
- magnetic means comprising magnetic material for magnetically coupling said valve mechanism with said fixation mechanism,
- wherein said fixation mechanism comprises an annular ring including magnetic material arranged as a substantially annular surface for coupling to a substantially similarly arranged annular surface of magnetic material provided to the valve mechanism for coupling the fixation mechanism with the valve mechanism, and further wherein the magnetic material is provided as a continuous annular ring of magnetic material.

* * * * *